United States Patent
Boggs, II et al.

(10) Patent No.: US 7,047,078 B2
(45) Date of Patent: May 16, 2006

(54) METHODS FOR STIMULATING COMPONENTS IN, ON, OR NEAR THE PUDENDAL NERVE OR ITS BRANCHES TO ACHIEVE SELECTIVE PHYSIOLOGIC RESPONSES

(75) Inventors: Joseph W. Boggs, II, Columbus, GA (US); Brian J. Wenzel, Cave Creek, AR (US); Kenneth J. Gustafson, Shaker Heights, OH (US); Warren M. Grill, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 65 days.

(21) Appl. No.: 10/662,055

(22) Filed: Sep. 12, 2003

(65) Prior Publication Data

US 2005/0060005 A1    Mar. 17, 2005

Related U.S. Application Data

(63) Continuation-in-part of application No. 10/113,828, filed on Mar. 29, 2002, now Pat. No. 6,907,293.

(60) Provisional application No. 60/280,222, filed on Mar. 30, 2001.

(51) Int. Cl.
*A61N 1/36* (2006.01)

(52) U.S. Cl. .............................. 607/41; 607/39; 607/2; 607/66

(58) Field of Classification Search .................... None
See application file for complete search history.

(56) References Cited

U.S. PATENT DOCUMENTS

| | | | |
|---|---|---|---|
| 3,727,616 A | 4/1973 | Lenzkes | |
| 3,870,051 A * | 3/1975 | Brindley | 607/40 |
| 3,941,136 A | 3/1976 | Bucalo | |
| 4,406,288 A | 9/1983 | Horwinski et al. | |
| 4,585,005 A * | 4/1986 | Lue et al. | 607/39 |
| 4,607,639 A | 8/1986 | Tanagho et al. | |
| 4,703,755 A | 11/1987 | Tanagho et al. | |
| 4,739,764 A * | 4/1988 | Lue et al. | 607/40 |
| 4,771,779 A | 9/1988 | Tanagho et al. | |
| 5,370,671 A * | 12/1994 | Maurer et al. | 607/41 |
| 5,454,840 A | 10/1995 | Krakovsky et al. | |
| 5,984,854 A | 11/1999 | Ishikawa et al. | |
| 6,061,596 A | 5/2000 | Richmond et al. | |
| 6,266,557 B1 | 7/2001 | Roe et al. | |
| 6,432,037 B1 | 8/2002 | Eini et al. | |

(Continued)

OTHER PUBLICATIONS

McNeal, D.R., B.R. Bowman (1985) Selective activation of muscles using peripheral nerve electrodes. Med. and Biol. Eng. and Comp. 23:249-253.

(Continued)

*Primary Examiner*—Kennedy Schaetzle
(74) *Attorney, Agent, or Firm*—Ryan Kromholz & Manion, S.C.

(57) ABSTRACT

Systems and methods control physiological functions of the urinary tract using at least one electrode sized and configured to be located on, in, or near a targeted component of the pudendal nerve. The systems and methods apply an electrical signal to the electrode at a selected frequency to stimulate the targeted component. The selected frequency is a first frequency or range of frequencies for achieving a first physiologic response (e.g., controlling urinary continence) and a second frequency or range of frequencies, different than the first frequency, for achieving a second physiologic response different than the first physiologic response (e.g., controlling micturition).

4 Claims, 4 Drawing Sheets

U.S. PATENT DOCUMENTS

| | | |
|---|---|---|
| 6,505,074 B1 | 1/2003 | Boveja et al. |
| 6,650,943 B1 | 11/2003 | Whitehurst et al. |
| 6,652,449 B1 | 11/2003 | Gross et al. |
| 6,735,474 B1 | 5/2004 | Loeb et al. |
| 6,836,684 B1 | 12/2004 | Rijkhoff et al. |
| 6,907,293 B1 | 6/2005 | Grill et al. |
| 6,941,171 B1 | 9/2005 | Mann et al. |
| 2002/0055761 A1 | 5/2002 | Mann et al. |
| 2002/0055779 A1 | 5/2002 | Andrews |
| 2003/0018365 A1 | 1/2003 | Loeb |
| 2003/0100930 A1 | 5/2003 | Cohen et al. |
| 2003/0114905 A1 | 6/2003 | Kuzma |
| 2004/0030360 A1 | 2/2004 | Eini et al. |
| 2004/0093093 A1 | 5/2004 | Andrews |
| 2004/0111126 A1 | 6/2004 | Tanagho et al. |
| 2004/0162594 A1 | 8/2004 | King |

OTHER PUBLICATIONS

Starbuck, D.L., (1965) Myo-electric control of paralyzed muscles. IEEE Transactions on Biomedical Engineering, 12(3):169-172, Jul.-Oct.

Starbuck, D.L., Mortimer, J.T., Sheally C.N., Reswick, J.B. (1966) An implantable electrodes system for nerve stimulation, Proc. 19th Ann. Conf. on Eng. in Med. and Biol. 8:38.

Sweeney, J.D., D.A. Ksienski, T.J. Mortimer (1990) A nerve cuff technique for selective excitation of peripheral nerve trunk regions, IEEE Trans. Biomed. Eng. 37:706-715.

Grill, W.M., J.T. Mortimer (1996) Quantification of recruitment properties of multiple contact cuff electrodes, IEEE Transactions on Rehabilitation Engineering 4(2):49-62.

Veraart, C., W.M. Grill, J.T. Mortimer (1993) Selective control of muscle activation with a multipolar nerve cuff electrode, IEEE Trans. Biomed. Engineering 40:640-653.

Caldwell, C. (1971) Multielectrode Electrical Stimulation of Nerve in Development of Orthotic Systems using Functional Electrical Stimulation and Myoelectric Control, Final Report Project # 19-P-58391-F-01, University of Lubljana, Faculty of Electrical Engineering, Lubljana, Yugoslavia.

McNeal, D.R. (1974) Selective stimulation in Annual reports of Progress, Rehabilitation Engineering Center, Rancho Los Amigos Hosipital, Downey, CA, pp. 24-25.

Wheeler et al.; "Bladder inhibition by penile nerve stimulation in spinal cord injury patients"; J Urol. Jan. 1992; 147(1):100-3.

Wheeler et al.; "Management of incontinent SCI patents with penile stimulation; preliminary results", J Am Paraplegia Soc. Apr. 1994; 17(2):55-0.

Grill, W.M., (2001) "Selective Activation of the Nervous System for Motor System Neutral Prostheses", in Intelligent Systems and Technologies in Rehabilitation Engineering, H.-N.L. Teodorescu, L.C. Jain, Eds., CRC Press, 211-241.

* cited by examiner

METHODS FOR STIMULATING COMPONENTS IN, ON, OR NEAR THE PUDENDAL NERVE OR ITS BRANCHES TO ACHIEVE SELECTIVE PHYSIOLOGIC RESPONSES

RELATED APPLICATIONS

This is a continuation-in-part of U.S. patent application Ser. No. 10/113,828, filed Mar. 29, 2002, now U.S. Pat. No. 6,907,293 entitled "Selectively Stimulating Components in, on, or near the Pudendal Nerve or its Branches to Achieve Selective Physiologic Responses," which claims the benefit of provisional U.S. patent application Ser. No. 60/280,222, filed Mar. 30, 2001, entitled "Systems and Methods for Selectively Stimulating Fascicles in the Pudendal Nerve to Achieve Selective Physiologic Responses."

FIELD OF THE INVENTION

This invention relates to systems and methods for stimulating nerves in animals, including humans.

BACKGROUND OF THE INVENTION

The lower urinary tract comprises the bladder, urethra, periurethral muscles and sphincters, and accessory organs. The lower urinary tract has two primary functions: the accumulation and storage of urine (continence), and the elimination of urine at an appropriate time (micturition or urination).

In able-bodied individuals, continence is maintained by low-pressure urine storage in a highly compliant bladder, augmented by tonic activity in the internal and external urethral sphincters. Micturition is achieved in such individuals by synergic relaxation of the urethral sphincter and contraction of the bladder.

Supra-sacral spinal cord injury, brainstem stroke, or disease (e.g., multiple sclerosis) can break or otherwise disrupt the path or paths by which electrical signals generated by the brain normally travel to neuromuscular groups in the lower urinary tract and elsewhere in the body. As a result, even though these nerves and muscles are intact, abnormal electrical signals or no electrical signals are received from the spinal cord, and the associated muscles do not function.

In the lower urinary tract, paralysis of the bladder may occur, and, with it, the inability to empty the bladder voluntarily. Loss of bladder control is a major, devastating effect of these conditions.

These conditions can also result in bladder hyper-reflexia, in which the bladder contracts spontaneously at small fluid volumes. Bladder sphincter dysynergia can also occur, in which the external urethral sphincter contracts, rather than relaxes, during bladder contractions. Hyper-reflexia and dysynergia lead to bladder contraction with high pressure, impaired voiding, large post-void residual volumes, and low bladder compliance.

These dysfunctions often lead to ureteric reflux and obstruction, infection of the kidneys, episodes of autonomic dysreflexia with dangerous rises in blood pressure, incontinence that leads to skin problems, frequent urinary tract infections, and long term renal damage. Urological complications are one of the leading causes of morbidity in persons with spinal cord injury. Loss of bladder control also has profound social impact and leads to decreased quality of life. It also leads to large direct medical costs of procedures, supplies, and medications.

Clean self-catheterization, sometimes in combination with anticholinergic agents, is presently the most effective way to treat the neurogenic bladder. This treatment, however, requires individuals with dexterity for catheterization, as well as tolerance for and response to the anticholinergic agents. Even with these individuals, urinary tract infections persist.

Restoration of bladder evacuation and continence has been achieved by electrical stimulation of the sacral nerve roots, coupled with surgical transections of sacral sensory nerve roots (dorsal rhizotomy). The dorsal rhizotomy eliminates bladder hyper-reflexia and bladder-sphincter dysynergia. This technology has resulted in documented medical, quality of life, and financial benefits. However, widespread application of this technology is limited because of the irreversible effects of the dorsal rhizotomy (which leads to loss of reflex erection in males) and the complex surgical implant procedure itself (which requires access through the back along the spine, laminectomies of vertebral bodies, and the risk of cerebrospinal fluid leaks and intradural infections).

Other, physical conditions also have adverse affects on day-to-day bladder function. For example, a condition called urge incontinence, for which there is sometimes no neurological cause found, results in a hyperactive bladder and a loss of continence. There is also a condition called stress incontinence, which can arise after muscle is stretched in the pelvis during childbirth. Bladder instability or dysfunction are also chronic conditions of many elderly people, especially women.

There is a need for systems and methods that can restore bladder and other urinary tract functions, e.g., micturition and/or continence, in a straightforward manner, without requiring self-catheterization, drug therapy, complicated surgical procedures, or irreversible surgical transections of nerve fibers.

SUMMARY OF THE INVENTION

The invention provides systems and methods for stimulating components of the pudendal nerve and/or its branches and/or its sacral roots in selected ways to control different desired physiological functions in the lower urinary tract.

According to one aspect of the invention, the systems and methods modulate the frequency of the stimulation waveform to thereby achieve significantly different physiologic responses. By modulating the frequency of the stimulation waveform, the same electrode or electrodes, having been selectively placed in a targeted region of the pudendal nerve, can serve to apply a stimulation waveform within a first selected frequency range to achieve a first desired result (e.g., to evoke bladder contractions), while serving to apply a stimulation waveform within a second selected frequency range to achieve a markedly different, second desired result (e.g., to inhibit bladder contractions).

According to another aspect of the invention, the systems and methods control different desired physiological functions in the lower urinary tract by stimulation of selected afferent nerve fibers in the deep perineal nerve and other branches of the pudendal nerve. In one embodiment, the waveforms are applied at different frequencies selected to generate different physiologic results, e.g., to evoke bladder contractions or to inhibit bladder contraction.

According to another aspect of the invention, the systems and methods operate to apply differing electrical signals that vary according to frequency, and/or amplitude, and/or waveform, to stimulate a targeted component to achieve a physiologic response, but at different levels of effectiveness (e.g., "mild," "medium," or "high"). In this arrangement, the systems and methods include a function that permits selection of a desired level of effectiveness and that generates an electric signal according to the selection to achieve the physiologic response at the desired level of effectiveness.

Other features and advantages of the inventions are set forth in the following specification and attached drawings.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

The various aspects of the invention will be described in connection with achieving the stimulation of targeted nerve components or fascicles within complex or compound nerve structures throughout the body. For the purpose of illustration, the invention will be disclosed in the context of the compound pudendal nerve trunk or its branches, to achieve desired physiological results in the lower urinary tract. That is because the features and advantages that arise due to the invention are well suited to this purpose. Still, it should be appreciated that the various aspects of the invention can be applied elsewhere in the body to achieve other objectives as well.

I. Anatomy of the Pudendal Nerve and Its Branches

Figure 1:
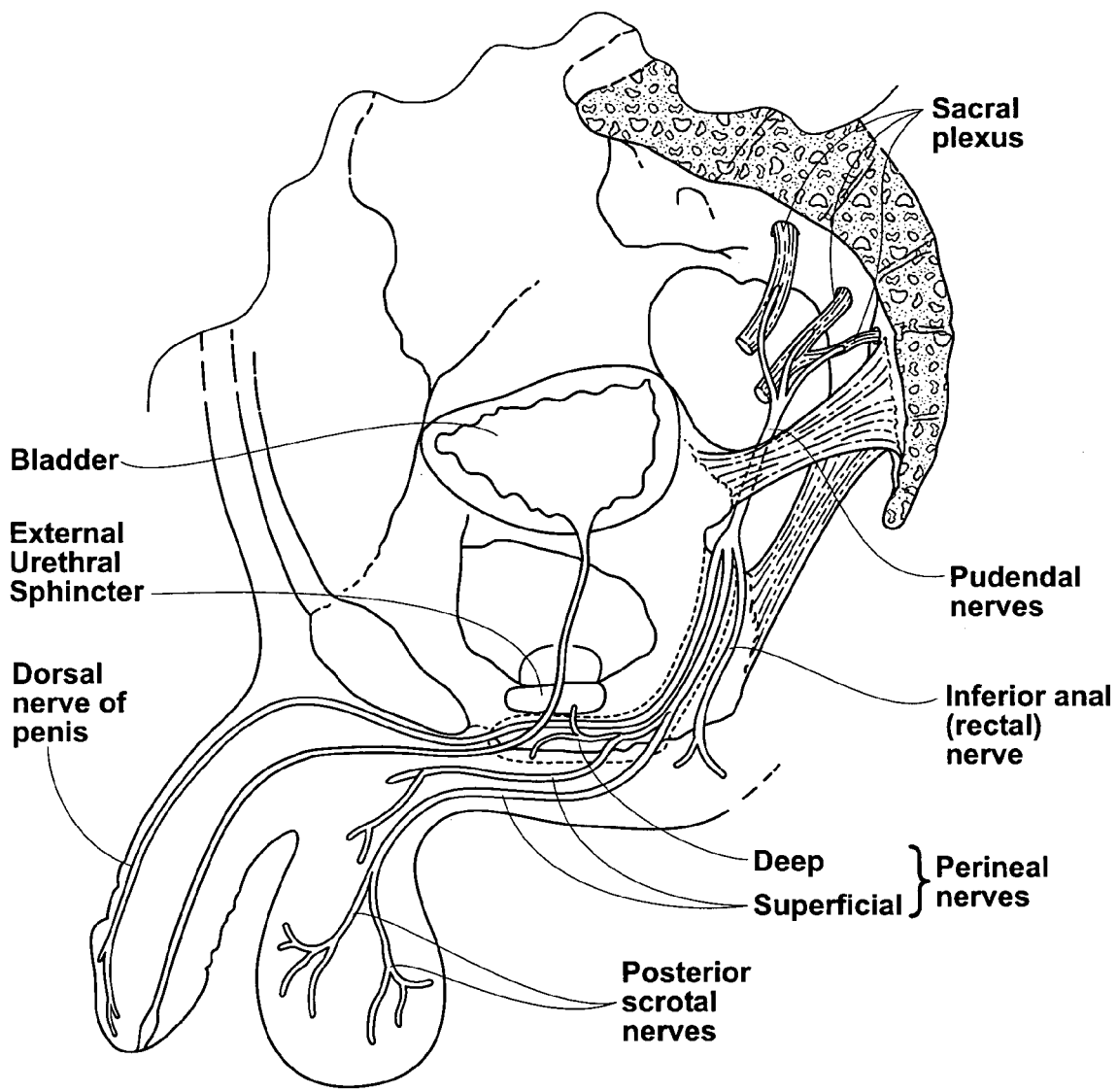
FIG. 1 is an anatomic view of the distribution of the pudendal nerve in a human male.

The pudendal nerve (see FIG. 1) is derived at the sacral plexus from the anterior devisions of the ventril rami of S2 through S4. The pudendal nerve accompanies the interior pudendal artery and leaves the pelvis through the greater sciatic foramen between the periformis and coccygeus muscles. It hooks around the ischial spine and sacrospinous ligament and enters the skin and muscles of the perineum, ending as the dorsal nerve of the penis or clitoris. The pudendal nerve is the main nerve of the perineum. FIG. 1 shows the distribution of the pudendal nerve in the male, but its distribution is similar in the female, because the parts of the female perineum are homologues of the male.

Figure 2:
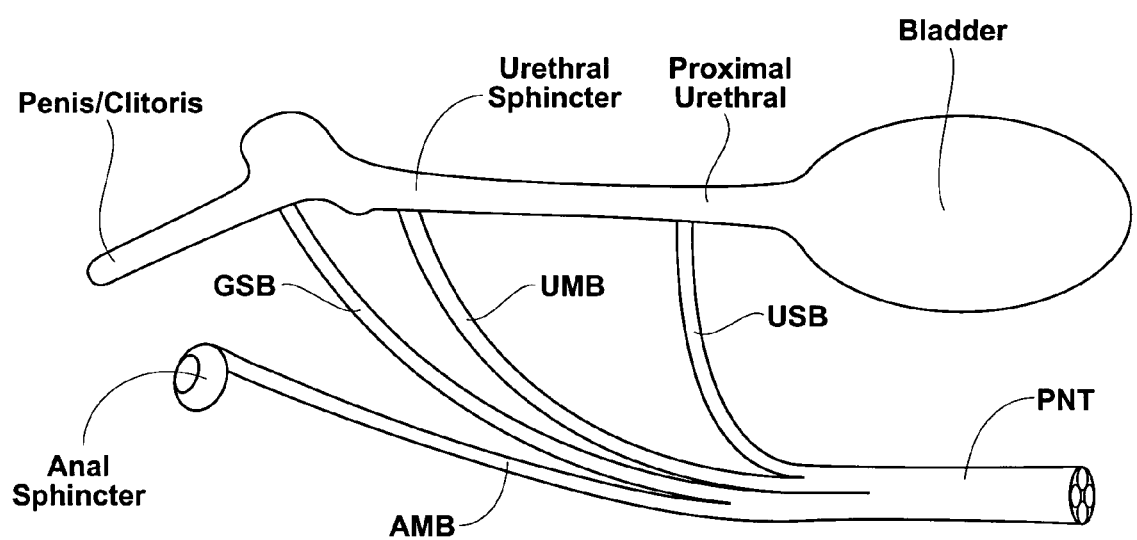
FIG. 2 is schematic view of the lower urinary tract and the pudendal nerve that innervates the organs and muscles of the lower urinary tract.

As FIG. 2 shows, the pudendal nerve trunk (PNT) carries afferent (sensory) and efferent (motor) nerve components that innervate muscles and organs in the lower urinary tract. FIG. 2 shows, in schematic form, the major branches of the pudendal nerve trunk (PNT).

Extending from the pudendal nerve are the genital sensory branch (GSB) and the urethral sensory branch (USB). The genital sensory branch (GSB) comprises the dorsal nerve of the penis in males and the clitoral nerve in females. The urethral sensory branch (USB) innervates the urethra.

Also extending from the pudendal nerve are the external urethral sphincter branch (UMB), which is also called the deep perineal branch, which innervates the external urethral sphincter, and the external anal sphincter branch (AMB), which is also called the inferior rectal branch, which innervates the external anal sphincter.

II. System Overview

Figure 3:
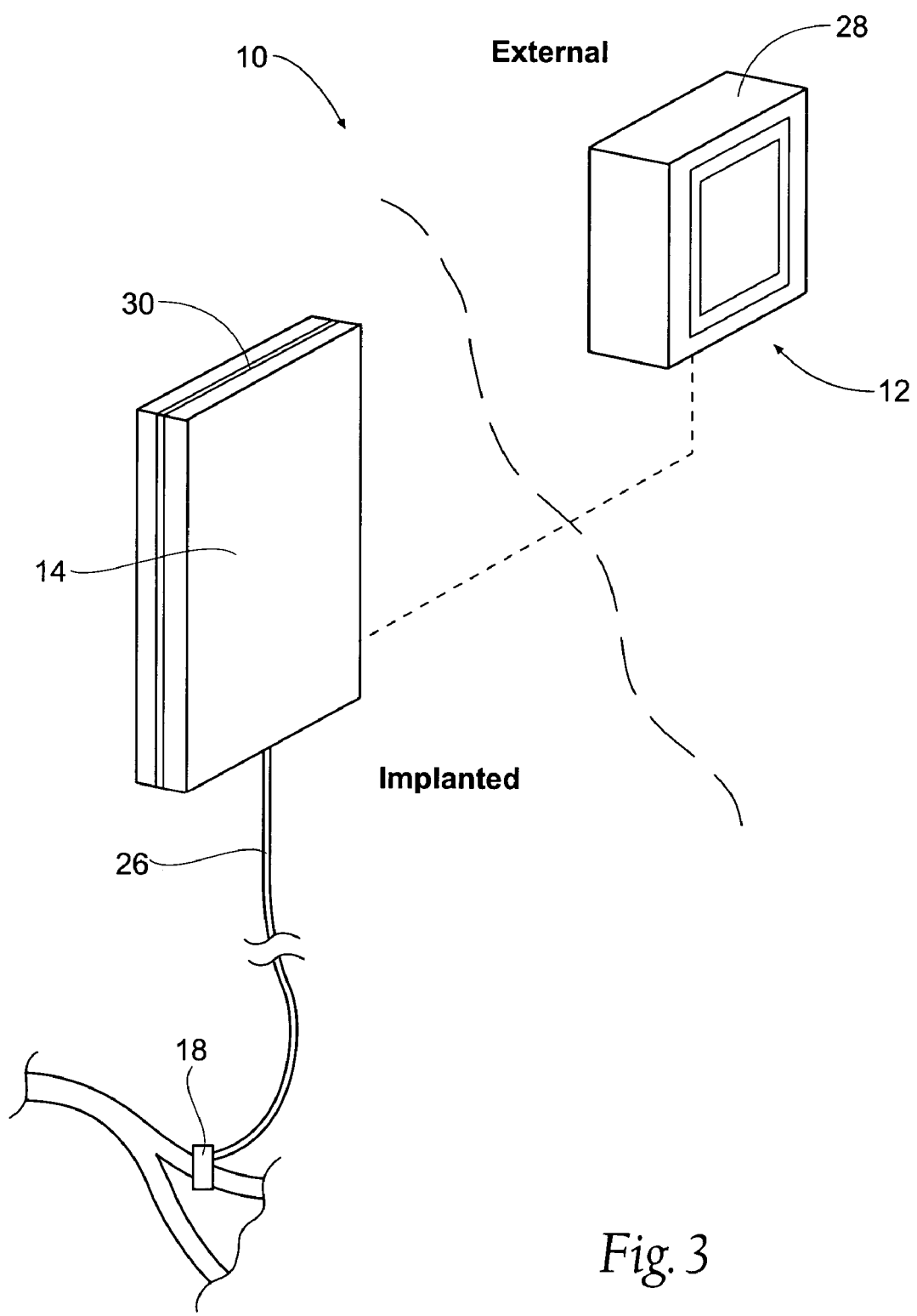
FIG. 3 is a schematic view of a system, which provides selective stimulation of the pudendal nerve and/or its branches and/or its sacral roots in selected ways to achieve either micturition, or continence, or both.

FIG. 3 shows a system 10 that makes possible the stimulation of components of the pudendal nerve and its branches in a selected fashion to control one or more desired physiological functions in the lower urinary tract.

As shown, the system 10 comprises four basic functional components including (i) a control signal source 12; (ii) a pulse generator 14; (iii) at least one electrode 18; and (iv) electrical leads 26 that couple the electrode 18 to the pulse generator 14. This arrangement allows the pulse generator 14 to be located remote from the electrode(s) 18, which— given the anatomy of the lower urinary tract—is desirable.

As shown in FIG. 3, the one or more electrodes 18 are sized and configured to be placed in, on or near the pudendal nerve, and/or its branch(es), and/or its spinal root(s). In the control of lower urinary tract function, particularly desirably anatomic regions for electrode placement include urethral afferents of the pudendal nerve and/or afferent nerve fibers in the deep perineal nerve, which (as FIG. 3 shows) is a branch of the pudendal nerve. FIG. 3 shows the latter placement of the electrode(s) 18.

As assembled and arranged in FIG. 3, the control signal source 12 allows the user to generate prescribed response demand inputs to the pulse generator 14. In the illustrated embodiment, the response demand inputs call for one or more desired urinary control functions—e.g., bladder contraction (for urination) and/or bladder inhibition (for urinary continence). The pulse generator 14 may include an on-board, programmable microprocessor 30, which carries embedded code. The code expresses pre-programmed rules or algorithms under which the desired electrical stimulation waveform is generated and distributed to the electrode(s) 18 in response to the prescribed demand inputs. According to these programmed rules, the pulse generator 14 directs prescribed stimulation waveforms through the lead(s) 26 to the electrode(s) 18, to stimulate selectively the targeted nerve or nerves and thereby achieve the desired physiologic function.

The system 10 desirably includes means for selectively modulating the frequency at which the stimulation waveforms are applied by the one or more electrodes 18. By modulating the frequency of the stimulation waveform, the same system components and placement of electrodes can serve to achieve markedly different physiologic responses. For example, the same system components and placement of electrodes can, by modulation of frequencies, either evoke bladder contractions, or inhibit bladder contractions, or accomplish both functions.

EXAMPLE 1

Stimulation of afferent nerve fibers in the deep perineal nerve and the pudendal nerve in cats generates robust bladder contractions at high stimulation frequencies (i.e., greater than about 15 Hz), with an optimal frequency being near about 33 Hz. However, stimulation of the same afferent nerve fibers in the deep perineal nerve and the pudendal nerve in cats at lower stimulation frequencies (i.e., equal to or below 10 Hz) (given the same amplitude for the waveform), inhibits bladder contractions, or at least has no effect.

EXAMPLE 2

Stimulation of the urethral afferent nerve in cats generates robust bladder contractions at low stimulation frequencies (i.e., less than or equal to 5 Hz). However (given the same amplitude for the waveform), stimulation of the same afferent nerves in cats inhibits bladder contractions or has no effect at higher stimulation frequencies (i.e., greater than 10 Hz).

Traditional views hold that coordinated micturition (bladder contractions coupled with a reduction in activity of the external urethral sphincter) requires a spinal-brainstem-spinal reflex loop that is triggered by bladder distension. The data of Examples 1 and 2 indicate that stimulation of the urethral sensory nerve branch (USB) and/or afferent nerve fibers in the deep perineal nerve within one selected frequency range can evoke a micturition-like bladder contraction, leading to low-pressure continuous stream evacuation of the bladder on demand. The data also indicate that stimulation of the same urethral sensory nerve branch (USB) and/or afferent nerve fibers in the deep perineal nerve at another selected frequency range can evoke an opposite result—a reduction in activity in the bladder.

EXAMPLE 3

Intra-urethral stimulation in men with complete spinal cord injury at higher amplitudes and higher frequencies is more effective at evoking bladder contractions. With 2 Hz stimuli, bladder contractions were evoked in ¾ trials at 5 mA, ¾ trials at 10 mA, and ⅚ trials at 20 mA, and with 20 Hz stimuli, bladder contractions were evoked in ¼ trials at 5 mA, ⅔ trials at 10 mA, and ½ trials at 20 mA.

The data in Example 3 show that, as a general proposition, higher stimulation waveform frequencies (i.e., 20 Hz) can be more effective in evoking bladder contractions in humans than lower stimulation waveform frequencies (i.e., 2 Hz).

The foregoing Examples 1, 2, and 3 demonstrate that—in systems that apply the waveforms using electrodes placed in, on or near the pudendal nerve, and/or its branch(es), and/or its spinal root(s), including urethral afferents of the pudendal nerve and/or afferent nerve fibers in the deep perineal nerve, and/or afferent nerve fibers located in the spinal roots—a desired physiologic response can be empirically correlated with the frequency of the stimulation waveform. Once the correlation has been established, frequency ranges or thresholds for bladder contraction and frequency thresholds or ranges for bladder inhibition can be identified and selected. Furthermore, the efficacy of the response can be further correlated with an optimal frequency or an optimal range of frequencies for identification and selection.

Having identified and selected the frequency thresholds or ranges based upon the correlation with desired physiologic results, the pulse generator 14 may be preprogrammed to provide a stimulation waveform at a selected frequency or range of frequencies depending upon the physiologic response desired. Alternatively, the pulse generator can include a manual-actuated switch or control knob which an operator operates or tunes to acquire a desired waveform frequency, given the desired physiologic response.

The shape of the waveform can vary. It can, e.g., be a typical square pulse, or possess a ramped shape. The pulse, or the rising or falling edges of the pulse, can present various linear, exponential, hyperbolic, or quasi-trapezoidal shapes. The stimulation waveform can be continuous, or it can be variable and change cyclically or in step fashion in magnitude and waveform over time.

Figure 4:
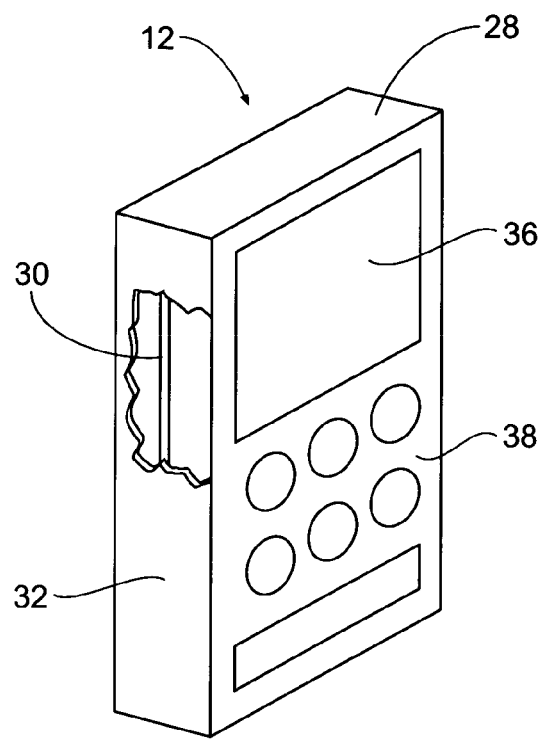
FIG. 4 is view of a manual controller that can be used in association with the system shown in FIG. 3, the manual controller including a microprocessor that enables a user interface.
Figure 5:
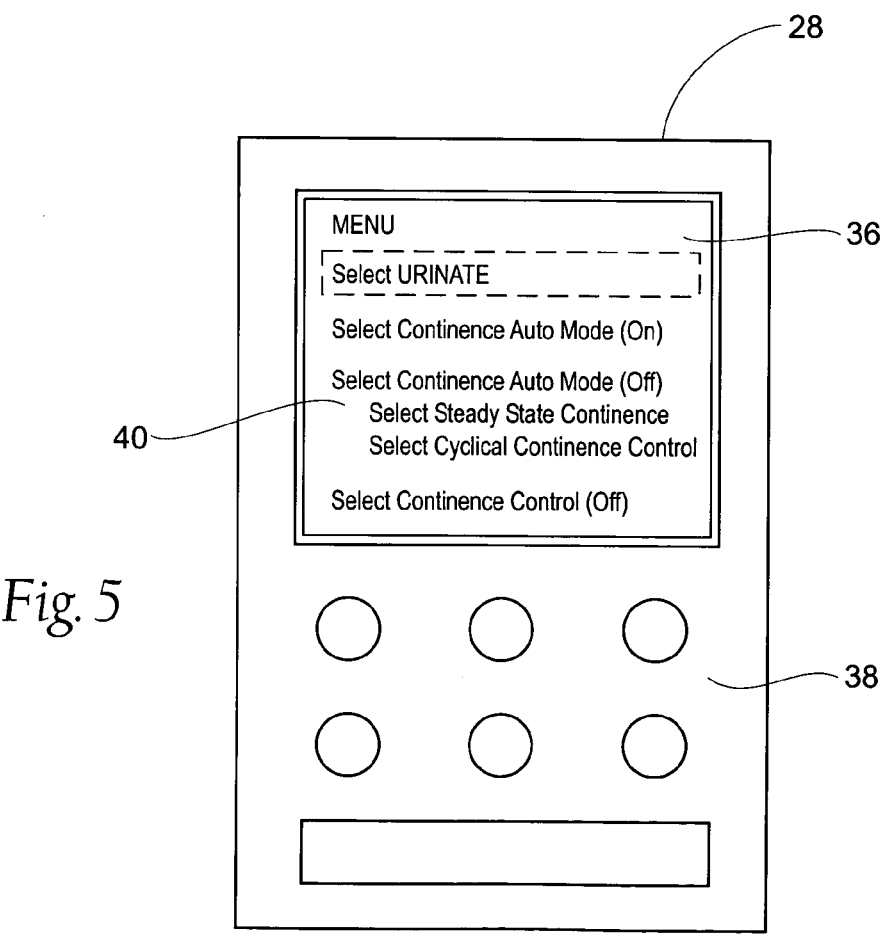
FIG. 5 is a view of a portion of the user interface that the manually controller shown in FIG. 4 can present to enable selection of different physiologic response using the system shown in FIG. 3.

For example, the control signal source 12 can comprise a manual controller 28 (see FIG. 4). Using the controller 28, the user can generate a "continence demand" input. In response, the pulse generator 14 applies electrical waveforms to the electrode 18 or electrodes at a first identified waveform frequency or range of frequency at which bladder function is inhibited, to stimulate the targeted nerve or nerves (e.g., urethral afferents of the pudendal nerve and/or afferent nerve fibers in the deep perineal nerve) to achieve the requested physiologic response. Using the manual controller 28, the user can also terminate a continence demand input. As a result, the user is able to "turn on" or "turn off" continence control, depending, e.g., upon the time of day or fluid consumption.

As another example, using the manual controller 28, the user can initiate a "micturition demand" input. In response, the pulse generator 14 applies electrical waveforms to the same electrode 18 or electrodes at a second identified waveform frequency or range of frequencies at which bladder contractions are generated, to stimulate the same targeted nerve or nerves to achieve a different physiologic response. Using the manual controller 28, the user can also terminate a micturition demand input. As a result, the user is able to urinate on demand.

The controller 28 may include the ability to select individual settings for levels of effectiveness for a specific response. These settings may be based on varying stimulation frequency, amplitude and/or waveform, to provide electrical signals that vary according to the level of effectiveness achieved. For example, to achieve bladder inhibition, "mild," "medium," and "high" settings may presented for selection, to achieve corresponding levels of bladder inhibition. "Mild" or "medium" settings may be less effective, but have advantages such as a prolonged battery life, longer chronic effectiveness without habituation, and less physical sensation.

As shown in FIG. 4, the manual controller 28 can be housed in a compact, lightweight, hand held housing 32, which desirable includes its own microprocessor 34 powered by a rechargeable, onboard battery (not shown). The microprocessor 34 carries embedded code which may include pre-programmed rules or algorithms that may govern operation of a display 36 and keypad 38, to create a user interface. The microprocessor 34 also expresses pre-programmed rules or algorithms under which desired demand inputs are selected and generated using the display 36 and the keypad 38. The microprocessor 34 can also have the capability to log data, and thereby keep a record of detection and stimulation that can be assessed by a physician.

As described, the system 10 applies the electrical signal(s)in response to a volitional act of an individual. Alternatively, the electrical signal(s) can be applied in a closed-loop fashion, automatically in response to a specific physiological signal or signals (e.g., electroneurogram or electromyogram) going above or below a predetermined limit, or in response to a sensed physiological event or events (e.g., bladder pressure or bladder volume) going above or below a predetermined limit, or a combination of one or more of these alone or in combination with volitional activation. The physiological signals or events can be sensed by the placement of at least one recording electrode in, on, or near a nerve, e.g., the pudendal nerve trunk or a branch or component of the pudendal nerve, or at least one recording electrode placed in, on, or near the bladder. The controller 28 can be pre-programmed to automatically select a "mild," "medium," or "high" setting based upon the nature of the physiologic signals sensed in the closed-loop system. These settings may also be determined by the sensing of physiologic signals in a closed loop system.

The basic functional components can be constructed and arranged in various ways. In one representative implementation, the electrode array 16, leads 26, and pulse generator 14 are all implanted. In this arrangement, the manual controller 28 comprises an external unit that is, e.g., magnetically coupled to the pulse generator 14, or coupled by a radio frequency link to the pulse generator 14 (e.g., in the manner as described in Peckham et al U.S. Pat. No. 5,167,229, which is incorporated herein by reference). Alternatively, a manual controller 28 can be coupled by percutaneous leads to the pulse generator 14.

Multiple electrodes 18, when used, can take the form of a peripherally spaced nerve cuff array implanted in, on, or near a compound nerve structure of the pudendal nerve trunk (PNT), and/or its branch(es), and/or its spinal root(s) to affect independent neural stimulation of nerve fascicles within the compound nerve structure. The array may be implanted without prior reference to the particular fascicles structure of the nerve, leading to a random orientation between electrodes and fascicles. Thus, programming or "tuning" will be required by a clinician to ascertain positions and operating parameters of electrodes in the array to bring about the desired stimulation of individual targeted fascicles. Alternatively, separate electrodes could be implanted in, on, or near the individual branches, thereby avoiding a random orientation. Techniques enabling sub-fascicular selection could also be employed.

Various features of the invention are set forth in the following claims.

We claim:

1. A method for controlling a physiological function comprising
    placing at least one electrode on, in, or near a targeted component of the pudendal nerve, and/or its branch(es), and/or its spinal root(s),
    selecting an electrical signal having an amplitude,
    applying the electrical signal at the selected amplitude to the electrode to selectively stimulate the targeted component, and
    without substantially changing the selected amplitude, selecting between a first frequency or range of frequencies to achieve a first desired physiologic response and a second frequency or range of frequencies to achieve a second desired physiologic response different than the first physiologic response.

2. A method according to claim 1
    wherein the targeted component comprises a urethral afferent of the pudendal nerve and/or afferent nerve fibers in the deep perineal nerve.

3. A method according to claim 1
    wherein the physiological function comprises one of controlling urinary incontinence and controlling micturition.

4. A method for controlling a physiological function of the lower urinary tract comprising
    placing at least one electrode on, in, or near afferent nerve fibers in the deep perineal nerve,
    selecting an electrical signal having an amplitude,
    applying the electrical signal at the selected amplitude to the electrode to selectively
    stimulate the afferent nerve fibers in the deep perineal nerve and
    without substantially changing the selected amplitude, selecting between a first frequency or range of frequencies to control urinary continence and a second frequency or range of frequencies different than the first frequency to control micturition.

* * * * *